United States Patent [19]

Payne

[11] Patent Number: 4,487,945

[45] Date of Patent: Dec. 11, 1984

[54] PREPARATION OF 2-EXO-HYDROXY-7-OXABICYCLO[2.2.1-]HEPTANES

[75] Inventor: George B. Payne, Modesto, Calif.

[73] Assignee: Shell Oil Company, Houston, Tex.

[21] Appl. No.: 559,512

[22] Filed: Dec. 8, 1983

Related U.S. Application Data

[63] Continuation-in-part of Ser. No. 414,548, Sep. 8, 1982, abandoned, which is a continuation-in-part of Ser. No. 331,095, Dec. 16, 1981, abandoned.

[51] Int. Cl.$^3$ ............................................. C07D 493/08
[52] U.S. Cl. ................................................... 549/463
[58] Field of Search ......................................... 549/463

[56] References Cited

U.S. PATENT DOCUMENTS 4,170,599 10/1979 Bennett .............................. 549/397

OTHER PUBLICATIONS

Wilson III, Charles W. et al., *Aust. J. Chem.*, 28, pp. 2539–2542 (1975).
MacRae, Ian C. et al., *Aust. J. Chem.*, 32, pp. 917–922 (1979).
Garside, J. Chem. Soc. (c), 1969, pp. 716–721.

*Primary Examiner*—Richard L. Raymond

[57] ABSTRACT

2-exo-Hydroxy-7-oxabicyclo[2.2.1]heptanes are prepared by treating the corresponding cis-epoxycyclohexanol with acid in an inert solvent or by treating a 3-cyclohexen-1-ol which will produce the corresponding cis-epoxy alcohol successively or concurrently with an oxidizing agent and an acid in an inert solvent.

18 Claims, No Drawings

PREPARATION OF 2-EXO-HYDROXY-7-OXABICYCLO[2.2.1]HEPTANES

CROSS-REFERENCE TO RELATED APPLICATIONS

This application is a continuation-in-part of Ser. No. 414,548, filed Sept. 8, 1982, now abandoned, which is a continuation-in-part of Ser. No. 331,095, filed Dec. 16, 1981, now abandoned.

BACKGROUND OF THE INVENTION

Field of the Invention

This invention is directed to a process for the preparation of 2-exo-hydroxy-7-oxabicyclo[2.2.1]heptanes.

SUMMARY OF THE INVENTION

The present invention relates to the preparation of a 2-exo-hydroxy-7-oxabicyclo[2.2.1]heptane by (a) treating the corresponding cis-epoxycyclohexanol with acid in an inert solvent to effect cyclization or (b) treating the corresponding 3-cyclohexen-1-ol successively or concurrently with an oxidizing agent and an acid in an inert solvent to effect epoxidation and cyclization and recovering a 2-exo-hydroxy-7-oxabicyclo[2.2.1]heptane.

The cyclization (ring closure) reaction (a) is surprising in its very high yield of the exo-hydroxy configuration of the resulting 7-oxabicyclo[2.2.1]heptan-2-ol. Many acids will catalyze this reaction, but a relatively strong acid, including mineral acids such as hydrochloric, sulfuric or sulfonic acids, or resin acid, such as Amberlyst sulfonic acid, is more suitable. Of these, sulfuric acid is preferred. Preferably, the acid has a $pK_A$ of 1 or less. In one embodiment, the acid is a sulfonic acid, including those of the alkyl or aryl type, such as methanesulfonic, ethanesulfonic, p-toluenesulfonic, m-nitrobenzenesulfonic, 2,4-dimethylbenzenesulfonic, benzenesulfonic acids, or the like. Of these, p-toluenesulfonic acid is preferred.

The reaction is preferably conducted by adding the acid to a cis-epoxy-alcohol, i.e., the cis-epoxycyclohexanol, contained in an inert solvent, ideally of the type also for use in the preparation of the cis-epoxy-alcohol. The acid is used in amounts between about 0.001 to about 0.5 mole per mole of cis-epoxycyclohexanol, suitably from about 0.01 to about 0.1, and preferably from about 0.02 to about 0.04 mole of acid per mole of cis-epoxycyclohexanol.

The solvent is an inert solvent such as chlorinated hydrocarbons, ethers, hydrocarbons, amides or the like. Suitable chlorinated hydrocarbons contain from 1 to 4 chlorine atoms in combination with an alkane chain containing from 1 to 4 carbon atoms or a benzene ring, for example, carbon tetrachloride, chloroform, dichloromethane, chlorobenzene and 1,2- or 1,3-dichlorobenzene and the like. Of the chlorinated hydrocarbons, methylene chloride is preferred. Ethers are generally those containing from 4 to 6 carbons, for example, diethyl ether, methyl tert-butyl ether, propylene oxide, dimethoxyethylene and diisopropyl ether and the like. Tetrahydrofuran and dioxane are also useful. Suitable alkanes contain from 5 to 10 carbon atoms, for example, n-pentane, n-hexane, n-heptane, n-octane, n-nonane, n-decane and their isomers. Petroleum fractions rich in alkanes are also suitable. Petroleum ether is also suitable. Cyclohexane and methylcyclohexane are examples of useful cycloalkane solvents containing from 6 to 8 carbon atoms. Suitable aromatic hydrocarbon solvents contain from 6 to 10 carbon atoms, for example, benzene, toluene, o-, m-, and p-xylene, the trimethylbenzenes, p-ethyltoluene and the like. In one embodiment, the solvent is a cycloalkane or aromatic hydrocarbon. Of these, toluene is preferred. Suitable amides include N,N-dimethylacetamide, dimethylformamide and the like.

The reaction is conducted at normal pressures and a temperature conveniently in the range of from about 0° C. to about 50° C. or slightly above. Generally, the temperature is from about 5° C. to about 40° C., preferably from about 10° C. to about 30° C.

The resulting 2-exo-hydroxy-7-oxabicyclo[2.2.1]heptane may be purified by conventional techniques or converted without isolation into useful ether derivatives.

Illustrative of the cis-epoxycyclohexanols which can be used in process (a) of the invention include compounds of the formula

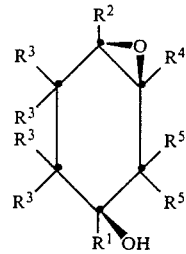

wherein
$R^2$ is a hydrogen atom; or a straight-chain alkyl group containing from 1 to 6 carbon atoms;
$R^1$ is a hydrogen atom; or is an alkyl group containing from 1 to 10 carbon atoms optionally substituted by up to 3 halogen atoms, each having an atomic number of from 9 to 35, inclusive, or by a hydroxy group, a cyano group or an alkoxy group containing from 1 to 6 carbon atoms, a $C_{1-6}$ alkylsulfonyl group, a $C_{6-10}$ arylsulfonyl group, a $C_{7-11}$ aralkylsulfonyl group, an azido group, a $C_{1-6}$ alkoxycarbonyl group, a hydroxycarbonyl group, a phosphoryl group, a phosphoryloxy group, an amine oxide group, a carbamoyl group or a thiocarbamoyl group in which each nitrogen atom is substituted by hydrogen or 1 or 2 alkyl groups containing from 1 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl or alkoxy group containing from 1 to 2 carbon atoms, each optionally substituted by one or more halogen atoms, each having an atomic number of from 9 or 17, or $R^1$ is a group $CO_2R^6$ or $CON(R^6)_2$ in which $R^6$ is a hydrogen atom, or an alkyl group containing from 1 to 6 carbon atoms;
each $R^3$ is independently selected from a hydrogen atom; a chlorine atom; a bromine atom; or an alkyl group containing from 1 to 4 carbon atoms, optionally substituted by up to 3 halogen atoms, each having an atomic number of from 9 to 35, inclusive; or two of $R^3$ when located on adjacent carbon atoms together form an epoxide ring or a carbon-carbon bond;

R$^4$ is a hydrogen atom; or an alkyl group containing from 1 to 4 carbon atoms optionally substituted by up to 3 halogen atoms having an atomic number of from 9 to 35, inclusive;

each R$^5$ is independently selected from a hydrogen atom; an alkyl group containing from 1 to 4 carbon atoms optionally substituted by up to 3 halogen atoms having an atomic number of from 9 to 35, inclusive; or hydroxy group; and stereoisomeric forms or mixtures thereof.

In an alternative process (b), a 3-cyclohexen-1-ol (substituted corresponding to the desired 2-exo-hydroxy-7-oxabicyclo[2.2.1]heptane) is treated successively with an oxidizing agent and an acid in an inert solvent. For example, a 1,4-disubstituted-3-cyclohexen-1-ol is converted principally into the corresponding cis-epoxy-alcohol of the formula below

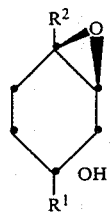

by action of an oxidizing agent and then cyclized by treatment with acid.

In process (b), the oxidizing agent is any oxidizing agent that will form the cis-epoxy-alcohol, and is preferably a peroxy acid, hydrogen peroxide or an organic hydroperoxide such as an alkyl or aralkyl hydroperoxide oxidizing agent, including organic peroxides such as m-chloroperbenzoic acid, peracetic acid, perphthalic acid, cumene hydroperoxide, persuccinic acid, pernonanoic acid, tert-butyl hydroperoxide (TBHP), persulfuric acid and hydrogen peroxide or equivalent epoxidizing reagents and peroxide generators. The oxidizing agent is perferably an organic hydroperoxide, especially tert-butyl hydroperoxide.

The oxidation with an alkyl hydroperoxide (TBHP) or with hydrogen peroxide is conducted in the presence of an appropriate vanadium catalyst present in an amount of from about 0.005 to about 0.10 mole of catalyst per mole of peroxide, preferably from about 0.01 to about 0.03 mole catalyst per mole of peroxide. The catalyst comprises vanadium metal, or a compound thereof. By compound is meant an organic or inorganic compound or complex. Vanadium compounds include oxides, acids, salts, halides, hydroxides, hydrated oxides, hydrides, carbonyls and the like, for example, including V$_2$O$_5$, ammonium metavanadate, n-butyl vanadate, vanadium naphthenate, vanadium stearate, vanadium sulfate, vanadium trichloride, vanadium oxychloride, vanadium hexacarbonyl and the like. Preferably, the catalyst is a complex, especially an organic complex, for example, with beta-diketones, o-hydroxy-benzaldehydes or o-hydroxybenzophenones and particularly with acetyl-acetone. While any of these catalysts can be used, vanadium(IV) bis (2,4-pentanedionate) oxide is preferred. The addition of an organic or inorganic alkaline material may be desirable in sufficient quantities to reduce or inhibit any tendency for the cis-epoxyalcohol to undergo a side reaction of acid hydrolysis to the corresponding triol. A variety of such materials are disclosed in U.S. Pat. No. 3,293,269, which is incorporated herein by references. Briefly, this patent discloses inorganic and organic alkaline material which do not need to be soluble in the reaction, including a variety of amines. Amines are convenient to use and include the primary, secondary and tertiary amines such as pyridine, n-butylamine, triethylamine and the like.

The oxidizing agent is usually used in amounts from about 1.0 to about 1.2 moles per mole of a (substituted) 3-cyclohexenol, preferably from about 1.0-1.1 moles per mole of a (substituted) 3-cyclo-hexenol.

The treatment with an oxidizing agent is conducted in an inert solvent, ideally of the type also useful in the subsequent cyclization as described above.

The reaction is conducted at normal pressures and temperatures conveniently in the range of from about $-10°$ C. to about 50° C. or slightly above. Generally, the temperature is from about $-5°$ C. to about 40° C., preferably from about 10° C. to about 30° C.

The reaction is usually conducted by forming a mixture of the alcohol and oxiding agent, preferably while agitating the reaction mixture, e.g. by stirring, and maintaining the desired reaction temperature. The resulting product cis-epoxy-alcohol may be purified by conventional techniques or converted without isolation into the 2-exo-hydroxy-7-oxabicyclo[2.2.1]heptane by cyclization as herein described.

Thus, a 1,4-disubstituted-3-cyclohexen-1-ol is converted mainly to 2-exo-hydroxy-1,4-disubstituted-7-oxabicyclo[2.2.1]heptane by treating it with an oxidizing agent, such as tert-butyl hydroperoxide, or m-chloroperbenzoic acid, and then a strong acid, such as p-toluenesulfonic acid. Especially useful for obtaining 2-exo-hydroxy-1,4-disubstituted-7-oxabicyclo[2.2.1]heptane is treatment of the cyclohexenol with (a) tert-butyl hydroperoxide and vanadium(IV) bis(2,4-pentanedionate) oxide as catalyst in methylene chloride or toluene, followed by treatment of the intermediate epoxide, preferably in situ, with sulfuric acid or a sulfonic acid, particularly p-toluenesulfonic acid. In some cases, acid generated during the epoxidation step from a peroxy acid, e.g. m-chloroperbenzoic acid, produces the desired product, 2-exo-hydroxy-7-oxabicyclo[2.2.1]heptane.

While it usually results in improved yields to conduct the epoxidation and ring closure steps successively, it is also possible to conduct them concurrently by treating the 3-cyclohexen-1-ol with a solution of oxidizing agent and acid. In such a concurrent process, the previously stated preferences of reagents and conditions usually apply.

Illustrative of the 3-cyclohexenols which can be used in process (b) of the invention include the compounds of formula

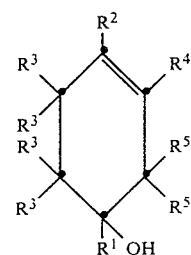

wherein $R^2$ is a hydrogen atom; or a straight-chain alkyl group containing from 1 to 6 carbon atoms;

$R^1$ is a hydrogen atom; or is an alkyl group containing from 1 to 10 carbon atoms optionally substituted by up to 3 halogen atoms, each having an atomic number of from 9 to 35, inclusive, or by a hydroxy group, a cyano group or an alkoxy group containing from 1 to 6 carbon atoms, a $C_{1-6}$ alkylthio group, a $C_{6-10}$ arylthio group, a $C_{7-11}$ aralkylthio group, an azido group, a $C_{1-6}$ alkoxycarbonyl group, a hydroxycarbonyl group, a phosphoryl group, a phosphoryloxy group, an amine group, a carbamoyl group or a thiocarbamoyl group in which each nitrogen atom is substituted by hydrogen or 1 or 2 alkyl groups containing from 1 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl or alkoxy group containing from 1 to 2 carbon atoms, each optionally substituted by one or more halogen atoms, each having an atomic number of from 9 or 17, or $R^1$ is a group $CO_2R^6$ or $CON(R^6)_2$ in which $R^6$ is a hydrogen atom, or an alkyl group containing from 1 to 6 carbon atoms;

each $R^3$ is independently selected from a hydrogen atom; a chlorine atom; a bromine atom; a cyano group; or an alkyl group containing from 1 to 4 carbon atoms optionally substituted by up to 3 halogen atoms, each having an atomic number of from 9 to 35, inclusive; or two of $R^3$ when located on adjacent carbon atoms together form an epoxide ring or a carbon-carbon bond;

$R^4$ is a hydrogen atom; or an alkyl group containing from 1 to 4 carbon atoms optionally substituted by up to 3 halogen atoms having an atomic number of from 9 to 35, inclusive;

each $R^5$ is independently selected from a hydrogen atom; or an alkyl group containing from 1 to 4 carbon atoms, optionally substituted by up to 3 halogen atoms having an atomic number of from 9 to 35, inclusive; or a hydroxy group; and stereoisomeric forms or mixtures thereof.

Illustrative of the 2-exo-hydroxy-7-oxabicyclo[2.2.1-]heptanes that can be prepared by process (a) or (b) include the compounds of formula I

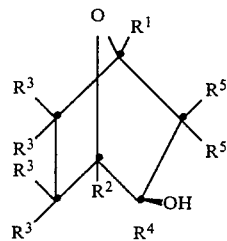

wherein $R^1$ is a hydrogen atom; or is an alkyl group containing from 1 to 10 carbon atoms optionally substituted by up to 3 halogen atoms, each having an atomic number of from 9 to 35, inclusive, or by a hydroxy group, a cyano group or an alkoxy group containing from 1 to 6 carbon atoms, a $C_{1-6}$ alkylsulfonyl group, a $C_{6-10}$ arylsulfonyl group, a $C_{7-11}$ aralkylsulfonyl group, an azido group, a $C_{1-6}$ alkoxycarbonyl group, a hydroxycarbonyl group, a phosphoryl group, a phosphoryloxy group, an amine oxide group, a carbamoyl group or a thiocarbamoyl group in which each nitrogen atom is substituted by hydrogen or by 1 or 2 alkyl groups containing from 1 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl or alkoxy group containing from 1 to 2 carbon atoms, each optionally substituted by one or more halogen atoms, each having an atomic number of from 9 or 17; or $R^1$ is a group $CO_2R^6$ or $CON(R^6)_2$ in which $R^6$ is a hydrogen atom, or an alkyl group containing from 1 to 6 carbon atoms;

$R^2$ is a hydrogen atom or a straight-chain alkyl group containing from 1 to 6 carbon atoms;

each $R^3$ is independently selected from a hydrogen atom; a chlorine atom; a bromine atom; or an alkyl group containing from 1 to 4 carbon atoms, optionally substituted by up to 3 halogen atoms, each having an atomic number of from 9 to 35, inclusive; or two of $R^3$ when located on adjacent carbon atoms together form an epoxide ring or a carbon-carbon bond;

$R^4$ is a hydrogen atom; or an alkyl group containing from 1 to 4 carbon atoms optionally substituted by up to 3 halogen atoms having an atomic number of from 9 to 35, inclusive;

each $R^5$ is independently selected from a hydrogen atom; an alkyl group containing from 1 to 4 carbon atoms, optionally substituted by up to 3 halogen atoms having an atomic number of from 9 to 35, inclusive; or a hydroxy group containing from 1 to 4 carbon atoms; and stereoisomeric forms thereof.

Because of their utility in preparing ether, preferred compounds of formula I are those wherein $R^2$ is a straight-chain alkyl group containing from 1 to 4 carbon atoms, $R^1$ is an alkyl group containing from 1 to 6 carbon atoms optionally substituted by up to 3 halogen atoms selected independently from fluorine, chlorine or bromine atoms or by OH, CN, an alkoxy group containing from 1 to 4 carbon atoms, a $C_{1-6}$ alkylsulfonyl group, a phenylsulfonyl group, a benzylsulfonyl group or is an aryl or aralkyl group each containing from 6 to 10 carbon atoms and 1 or 2 carbon atoms in any alkyl portion, optionally substituted by one or more substituents independently selected from a halogen atom having an atomic number of from 9 to 35, inclusive, or by an alkyl or alkoxy group containing from 1 to 2 carbon atoms each optionally substituted by one or more halogen atoms having an atomic number of from 9 or 17, and each $R^3$, $R^4$ and $R^5$ is a hydrogen atom.

More preferably, in the compounds of Formula I above, $R^1$ is a hydrogen atom or an alkyl group containing from 1 to 3 carbon atoms optionally substituted by chlorine, for example, a methyl, ethyl, n-propyl, isopropyl or 1-chloro-1-methylethyl group. A further preferred subclass of the invention is when $R^2$ is an alkyl group containing from 1 to 2 carbon atoms, i.e. a methyl or ethyl group and $R^1$ is an alkyl group containing from 1 to 3 carbon atoms, e.g. a methyl, ethyl, n-propyl, or isopropyl group. Compounds wherein $R^2$ is a methyl group and $R^1$ is an isopropyl group are one preferred subclass, compounds wherein $R^2$ and $R^1$ each is an ethyl group are another preferred subclass and compounds wherein $R^2$ is methyl and $R^1$ is 1-chloro-1-methylethyl group are also another preferred subclass.

Each $R^3$ is preferably independently a hydrogen atom; a chlorine atom; a bromine atom; or an alkyl group containing 1 to 2 carbon atoms, i.e. a methyl or ethyl group. A further preferred subclass of the invention is when each $R^3$ is a hydrogen atom;

Preferably, $R^4$ is a hydrogen atom;

Preferably, each $R^5$ is a hydrogen atom or an alkyl group containing 1 or 2 carbon atoms, i.e. a methyl or ethyl group. A further preferred subclass is when each $R^5$ is a hydrogen atom.

Non-limiting examples of compounds prepared by the processes of the invention include:

2-exo-hydroxy-1,4-dipropyl-7-oxabicyclo[2.2.1]heptane, 2-exo-hydroxy-1,4-dibutyl-7-oxabicyclo[2.2.1]heptane, 2-exo-hydroxy-1,4-diethyl-7-oxabicyclo[2.2.]heptane, 2-exo-hydroxy-1-methyl-4-(1-methyl-1-cyanoethyl)-7-oxabicyclo[2.2.1]heptane, 2-exo-hydroxy-4-hexyl-7-oxabicyclo[2.2.1]heptane, 2-exo-hydroxy-1-methyl-4-(1-methoxy-1-methylethyl)-7-oxabicyclo[2.2.1]heptane, 2-exo-hydroxy-1-methyl-4-hexyl-7-oxabicyclo[2.21]heptane, 2-exo-hydroxy-1-ethyl-4-isobutyl-7-oxabicyclo[2.2.1]heptane, 2-exo-hydroxy-1-ethyl-4-isopropyl-7-oxabicyclo[2.2.1]heptane, 2-exo-hydroxy-1-methyl-4-isopropyl-7-oxabicyclo[2.2.1]heptane, 2-exo-hydroxy-5,6-dichloro-1,4,5,6-tetramethyl-7-oxabicyclo[2.2.1]heptane, 2-exo-hydroxy-5,6-dibromo-1,4-diethyl-7-oxabicyclo[2.2.1]-heptane, 2-exo-hydroxy-1-methyl-4-(1-methyl-1-phenoxyethyl)-7-oxabicyclo[2.2.1]heptane, 2-exo-hydroxy-1-methyl-4-benzyl-7-oxabicyclo[2.21]heptane, 2-exo-hydroxy-1-methyl-4-(1methyl-1-(dimethylaminoethyl)-7-oxabicyclo[2.2.1]heptane N-oxide, 2-exo-hydroxy-1,4-dimethyl-5,6-epoxy-7-oxabicyclo[2.2.1]-heptane, 2-exo-hydroxy-1,2-dimethyl-4-isopropyl-7-oxabicyclo[2.2.1]-heptane, 2-exo-hydroxy-1,3,3,4-tetramethyl-7-oxabicyclo[2.2.1]heptane, 2-exo-hydroxy-1,3,3-trimethyl-4-isopropyl-7-oxabicyclo[2.2.1]heptane, 2-exo-hydroxy-1,3,3-trimethyl-7-oxabicyclo[2.2.1]heptane, 2-exo-hydroxy-1-methyl-4-(methoxycarbonyl)-7-oxabicyclo[2.2.1]heptane, 2-exo-hydroxy-1-methyl-4-cyano-7-oxabicyclo[2.2.1]heptane, 2-exo-hydroxy-1,4-dimethyl-5-cyano-7-oxabicyclo[2.2.1]-heptane, 2-exo-hydroxy-1,4-dimethyl-6-cyano-7-oxabicyclo[2.2.1]-heptane, 2-exo-hydroxy-1,4-dimethyl-5-(ethoxycarbony)-7-oxabicyclo[2.2.1]heptane, 2-exo-hydroxy-1,4-dimethyl-6-(ethoxycarbonyl)-7-oxabicyclo[2.2.1]heptane, 2-exo-hydroxy-1,4-dimethyl-5,6-dimethoxy-7-oxabicyclo[2.2.1]heptane, 2-exo-hydroxy-1,4-dimethyl-3-methoxy-7-oxabicyclo[2.2.1]heptane, 2-exo-hydroxy-4-(1-carboxy-1-methylethyl)-1-methyl-7-oxabicyclo[2.2.1]heptane, 2-exo-hydroxy-4-(1-methoxycarbonyl-1-methylethyl)-1-methyl-7-oxabicyclo[2.2.1]heptane, 2-exo-hydroxy-4-(1-(N,N-dimethylcarbamoyl)-1-methylethyl)-1-methyl-7-oxabicyclo[2.2.1]heptane, 2-exo-hydroxy-4-(1-azido-1-methylethyl)-1-methyl-7-oxabicyclo[2.2.1]heptane, 2-exo-hydroxy-4-(1-bromo-1-methylethyl)-1-methyl-7-oxabicyclo[2.2.1]heptane.

The 2-exo-hydroxy-7-oxabicyclo[2.2.1]heptanes exhibit geometrical and optical isomerism and may be prepared in optically active and/or geometrical forms, which may be mixed, or as racemates, which may subsequently be resolved into optically active and/or geometrical forms. The various optical and geometrical forms and various combinations thereof of ethers prepared from the materials of the invention usually have different herbicidal activities. The materials of formula I that have the OH group exo (formula Ia below) with respect to the oxygen-containing bridge result in exo ethers usually more herbicidally active than the ethers of the endo hydroxy form (formular Ib below) or the exo-endo mixture.

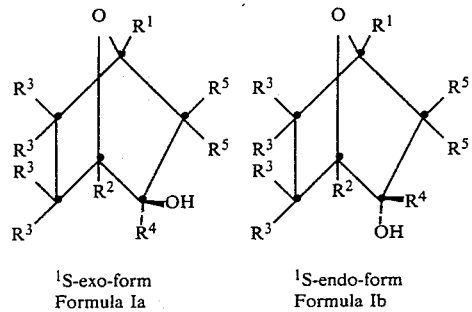

$^1$S-exo-form
Formula Ia $^1$S-endo-form
Formula Ib

When $R^2$ is hydrogen, then the compounds of formulas Ia and Ib have the 1S absolute configuration shown above. Such compounds of the invention of Ia that correspond in configuration are preferred. In situations where the endo form is desired it can be obtained by oxidation of the 2-exo-hydroxy compound to the corresponding ketone followed by reduction of the ketone with sodium borohydride.

The 2-exo-hydroxy-7-oxabicyclo[2.2.1]heptanes are useful intermediates to the corresponding novel ethers having herbicidal properties in which the hydrogen of the 2-hydroxy group is replaced by a group $WCH_2-$ in which W is an optionally-substituted, unsaturated, aromatic or heteroaromatic group including alkenyl, alkynyl, phenyl, furyl, pyridyl, cyclohexenyl, naphthyl, pyrrolyl, azacyclopentadiene, (is)oxazolyl, triazinyl, thiazolyl, imidazolyl and the like. These ethers and their use to control the growth of unwanted plants are disclosed in the copending U.S. patent application Ser. No. 331,094, filed Dec. 16, 1981, the disclosures of which application are incorporated by reference. As discussed in the reference application, the ethers are prepared by treating the 2-exo-hydroxy-7-oxabicyclo[2.2.1]heptane with a compound of the formula $WCH_2X$ in which X is a halogen atom, such as bromine, chloride or iodine or is a mesyloxy, tosyloxy group or the like, preferably in the presence of a strong base and an inert diluent, and preferably in the presence of a catalyst. The strong base is suitably an alkali metal hydride, amide, hydroxide or carbonate, including, for example, sodium hydride, sodium amide, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, toluene, methylene chloride and the like. Suitable catalysts are organic bases, such as tertiary amines and ammonium compounds, for example, triethylamine, benzyltriethylammonium chloride and the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

The 3-cyclohexen-1-ols, useful for the preparation of Compound I, can be synthesized as described below or obtained from natural sources.

(a) Where $R^2$ is methyl and $R^1$ is isopropyl, and the remaining R's are hydrogen, the compound is terpinen-4-ol, which occurs naturally. Terpinen-4-ol is converted to 2-exo-hydroxy-1-methyl-4-isopropyl-7-oxabicyclo[2.2.1]heptane by treatment with an oxidizing agent, for example, a peroxide such as m-chloroperbenzoic acid, peracetic acid or tert-butyl hydroperoxide. The optical configuration of terpinen-4-ol is retained in the reaction. Thus, ($\pm$), ($-$) or ($+$) 2-exo-hydroxy-1-methyl-4-isopropyl-7-oxabicyclo[2.2.1]heptane can be obtained. 2-endo-Hydroxy-1-methyl-4-isopropyl-7-oxabicyclo[2.2.1]heptane is known from Garside et al., J. Chem. Soc., page 716–721 (1969). 2-exo- and endo-Hydroxy-1-methyl-4-isopropyl-7-oxabicyclo[2.2.1]heptanes are converted to the ethers of the invention as described above. Although terpinen-4-ol occurs in nature in optically active and racemic forms, it can also be prepared by epoxidation of terpinolene, e.g. with peracetic acid in methylene chloride, followed by reduction of the epoxide, e.g. with sodium diethylaluminum hydride in tetrahydrofuran.

(b) Substituted-1-oxaspiro(2.5)oct-5-enes are useful for preparing 3-cyclohexen-1-ols where $R^1$ is substituted by OH, OR, SR, $NR_2$, $N_3$, $P(O)(OR)_2$. Treatment of a 1-oxaspiro(2.5)oct-5-ene with water or an alcohol in the presence of a strong acid affords the corresponding 3-cyclohexen-1-ol substituted in the 1-position by a hydroxymethyl or alkoxymethyl group. Treatment of 1-oxaspiro(2.5)oct-5-ene with thiophenol, or an alkyl, $C_{6-11}$ aryl, or $C_{7-11}$ aralkyl mercaptan, in the presence of a catalyst, such as sodium hydride, and a suitable solvent, produces correspondingly a thio-substituted 3-cyclohexen-1-ol that can be converted to the corresponding sulfonyl derivative in the course of the oxidation process described above. Where $R^1$ is halo-substituted, the haloalkyl-substituted-3-cyclohexen-1-ol is prepared by treating a spiro compound as defined above with an ethereal hydrohalogenic acid, e.g. hydrochloric acid. The resulting halo-substituted-3-cyclohexen-1-ol is converted to the desired ether of the invention as described above. The (chloroalkyl)-substituted ethers of the invention made by treatment of the spiro compound with HX in which X is halogen can then be dehydrochlorinated to yield the corresponding 4-alkenyl-substituted ethers of the invention (where $R^1$ is alkenyl) with the use of a base. Compounds where $R^1$ is alkenyl are also made by rearrangement of the spiro compounds upon treatment with protic or Lewis acids. Where $R^1$ is substituted by an amine oxide group, a spiro compound as defined above is treated with the appropriate dialkylamine in the presence of a catalyst such as triethylaluminum; the subsequent epoxidation step produces the amine oxide. Where $R^1$ is dialkoxyphosphoryl, the compounds may be prepared by treatment of a 1-oxaspiro[2.5]oct-5-ene with the appropriate phosphite ester.

(c) Preparation of 3-cyclohexen-1-ols can be effected from p-substituted phenols in which the substituent group corresponds to R in the formula I of the invention by procedures of the literature for the Birch-type reduction of derivatives of benzene, many of which are detailed in Rodd's Chemistry of Carbon Compounds, Second Edition, Vol. II, Part B, pages 1–4 (1968). In an example, a p-substituted phenol is first methylated to protect the hydroxy group yielding the corresponding p-alkylanisole. This p-alkylanisole is treated with a reducing agent such as lithium-ammonia or sodium-ammonia and the resulting product is hydrolyzed to yield the corresponding 4-substituted-3-cyclohexen-1-one. Treatment of this ketone with an appropriate organometallic (Grignard) reagent, $R^1MgBr$ or $R^1Li$ in which $R^1$ corresponds to that in the formula I of the invention and is alkyl or alkenyl, e.g. at 20°–60° C. in the presence of anhydrous ethers, yields the desired 1,4-disubstituted-3-cyclohexen-1-ol intermediate. The 4-substituted-3-cyclohexen-1-one can also be reduced, e.g. by hydrides, to the corresponding 3-cyclohexen-1-ol unsubstituted in position-4. When $R^1$ is alkenyl, this double bond can be treated (after ring closure) with HX or $X_2$ in which X is chlorine or bromine, or with RSH in which R is $C_{1-6}$ alkyl, phenyl or benzyl to give differently substituted products.

Where $R^1$ is substituted by CN, a 4-substituted-3-cyclohexen-1-one is treated with an alpha-bromoalkanenitrile in the presence of zinc dust. The resulting 1-hydroxy-alpha,alpha,4-trisubstituted-3cyclohexenacetonitrile is cyclized.

Where $R^1$ is $CO_2R^6$, $CON(R^6)_2$, CN, as well as alkyl, the 3-cyclohexen-1-ols can be prepared starting from suitable Diels-Alder adducts. For example, methyl pyruvate is converted by known procedures to its enol acetate and the latter is treated with isoprene to produce a Diels-Alder adduct. Hydrolysis of the acetate function affords 1-hydroxy-4-methyl-3-cyclohexene-1-carboxylic acid methyl ester, which can be converted to compounds of the invention by the epoxidation-cyclization procedures described above. Treatment of compounds of the invention where $R^1$ in I is methoxycarbonyl with ammonia gives the $CON(R^6)_2$ compound where $R^6=H$, and dehydration of the latter with thionyl chloride affords the compound of the invention where $R^1$ is cyano.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

(±)-2-exo-Hydroxy-1-methyl-4-isopropyl-7-oxabicyclo[2.2.1]heptane

To a solution of 30.8 g of (±)-terpinen-4-ol and 0.8 g of vanadium (IV) bis(2,4-pentanedionate) oxide in 300 ml of methylene chloride was added 22.0 g of 90% tert-butyl hydroperoxide. The resulting reaction, initially mildly exothermic, was held at reflux for 2 hours, after which 0.8 g of p-toluenesulfonic acid in 10 ml of glyme was added. The resulting reaction mixture was refluxed for an additional 1.5 hours, cooled and 0.8 g of anhydrous sodium acetate was added with stirring. After filtration, the filtrate was concentrated and Claisen distilled to give 28.4 g of the desired product, b.p. 80°–95° C. (2 mm).

EMBODIMENT 2

(±)-2-exo-(Benzyloxy)-1methyl-4-isopropyl-7-oxabicyclo[2.2.1]heptane

To a solution of 1.7 g of (±)-2-exo-hydroxy-1-methyl-4-isopropyl-7-oxabicyclo[2.2.1]heptane in 15 ml of dimethylformamide was added at room temperature 0.5 g of 50% sodium hydride. The resulting mixture was stirred overnight at room temperature, heated for one-half hour at 50° C., cooled to room temperature, and after 1.5 g of benzyl chloride was added in one portion, stirred at room temperature for three hours, heated to 50° C. for one hour, cooled, poured into 50 ml of water, and extracted with one 50 ml and two 25 ml portions of methylene chloride. The combined methylene chloride extracts were washed with 100 ml of water, dried and evaporated to give an orange oil. Claisen distillation yielded 1.5 g of the desired product, b.p. 103° C. at 0.08 mm.

EMBODIMENT 3

4-Ethyl-3-cyclohexen-1-one

To a stirred refluxing mixture of 600 ml of dry ether and 1600 ml of liquid ammonia was added 136 g of p-ethylanisole. After 15 minutes, there was added portionwise, at −35° to −32° C., a 26.4 g quantity of lithium ribbon over 0.5–1 hour. After an additional 15 minutes, 193 g of dry ethanol was added dropwise at −35° to −32° C. Stirring was continued until the blue color disappeared, and the ammonia was allowed to evaporate on standing overnight. The residue was poured into 1 l of ice water and extracted twice with ether. The combined ether extracts concentrated to a volume of about 300 ml was stirred with 250 ml of water containing 46 g of oxalic acid overnight at ambient temperature. This mixture was diluted with 1 liter of water and extracted twice with ether. The combined ether extracts were washed with 5% sodium bicarbonate and then with water. After drying, the ether solution was vacuum-concentrated to a residue of 104.4 g of desired product; it was 94% pure by GLC analysis and used without distillation.

EMBODIMENT 4

1,4-Diethyl-3-cyclohexen-1-ol

To a stirred solution of 35 ml of 3.2M ethereal ethyl magnesium bromide (Aldrich) in 75 ml of dry ether was added dropwise at gentle reflux a solution of 10.0 g of 4-ethyl-3-cyclohexen-1-one in 25 ml of ether. After one hour longer at reflux, the mixture was cooled and treated dropwise with 80 ml of water. The aqueous layer was extracted with ether and the combined ether layers were dried, concentrated, and Claisen-distilled to give 7.3 g of the desired product, b.p. 82°–86° C. (5 mm).

EMBODIMENT 5

(±)-2-exo-Hydroxy-1,4-diethyl-7-oxabicyclo[2.2.1]heptane

To a stirred solution of 15.4 g of 1,4-diethyl-3-cyclohexen-1-ol and 0.4 g of vanadium(IV) bis(2,4-pentanedionate) oxide in 125 ml of methylene chloride was added dropwise at gentle reflux 11.0 g of 90% tert-butyl hydroperoxide. After an additional 2 hrs. reflux, the mixture was cooled slightly, treated with 7.2 ml of glyme containing 0.58 g of p-toluenesulfonic acid, and refluxed for 2 hr longer. The cooled mixture was stirred for 0.5 hr with 1.0 g of anhydrous sodium acetate and filtered through filter aid. The filtrate was concentrated and Claisen-distilled to give 14.4 g of product, b.p. 65°–78° C. (1 mm).

EMBODIMENT 6

(±)-2-exo-Benzyloxy-1,4-diethyl-7-oxabicyclo[2.2.1]heptane

A stirred mixture of 3.8 g of crude (±)-2-exo-hydroxy-1,4-diethyl-7-oxabicyclo[2.2.1]heptane, 50 ml of N,N-dimethylacetamide and 1.0 g of sodium hydride (washed with n-hexane) was warmed slowly to 80° C. to complete hydrogen evolution. The cooled mixture was treated with 3.0 g of benzyl chloride, again warmed to 80° C., poured into ice water, and extracted twice with methylene chloride. The combined organic extracts were washed, dried, concentrated and Claisen-distilled to give 2.6 g of the desired product, b.p. 105°–110° (0.1 mm).

EMBODIMENTS

By procedures similar to those in Embodiments 1 and 5, the following compounds of the invention in Table I below were prepared.

TABLE I

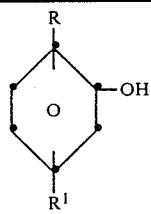

| Embodiment | R | R¹ | Rotation and Configuration | Boiling Point, °C. (mm) |
|---|---|---|---|---|
| 6 | $C_2H_5$ | $CH_3$ | (+) exo | 72–74 (1.5) |
| 7 | $CH_3$ | $C_2H_5$ | (+) exo | 84–105 (2) |
| 8 | $CH_3$ | $CH_3$ | (+) exo | 80–87 (5) |
| 9 | $CH_3$ | $n\text{-}C_4H_9$ | (+) exo | 95–100 (1.5) |
| 10 | $n\text{-}C_3H_7$ | $CH_3$ | (+) exo | 74–76 (1) |

TABLE I-continued

|  |  |  | Rotation and | Boiling Point, |
|---|---|---|---|---|
| Embodiment | R | R¹ | Configuration | °C. (mm) |
| 11 | $CH_3$ | phenyl | (+) exo | 112–118 (0.15) |

The above alcohols in Table I were converted to the corresponding benzyl ethers by procedures similar to those described in Embodiments 2 and 6 above.

EMBODIMENT 12

4-Methyl-1-(1-methyl-1-(phenylthio)ethyl)-3-cyclohexen-1-ol

To a stirred solution of 76 g of 2,2,6-trimethyl-1-oxaspiro(2.5)oct-5-ene in 300 ml of n-pentanol were added 2.0 g of 60% sodium hydride and 60 g of thiophenol. After 18 hours reflux, the mixture was vacuum concentrated at 90°–95° C. The residue was dissolved in methylene chloride and washed twice with 2N sodium hydroxide. The dried solution was Claisen-distilled to give 106 g of crude product, b.p. 120°–125° C. Recrystallization from 250 ml of hexane gave 69.1 g of the desired product, m.p. 73°–74° C.

EMBODIMENT 13

(±)-2-exo-Hydroxy-1-methyl-4-(1-methyl-1-(phenylsulfonyl)ethyl)-7-oxabicyclo[2.2.1]heptane To a stirred solution of 13.1 g of (±)-4-methyl-1-(1-methyl-1-(phenylthio)ethyl)-3-cyclohexen-1-ol and 0.27 g of vanadium(IV) bis(2,4-pentanedionate) oxide in 130 ml of methylene chloride was added dropwise at reflux 20.0 g of 90% tert-butyl hydroperoxide in 10 minutes. The mixture was refluxed for one hour longer, and after cooling, washed, dried and vacuum-concentrated at 50°–55° C. To the resulting residue of about 18 g 5 ml of glyme containing 0.4 g of p-toluenesulfonic acid was added. The mixture was stirred overnight at 5°–25° C. Since an insoluble oil had formed, 100 ml of chloroform was added and the ether and pentane were removed by vacuum-concentration. The residual chloroform solution was washed with potassium carbonate, dried and concentrated to a residue of 14.9 g. This residue was purified by dry column chromatography using a 30:220:500 mixture of tetrahydrofuran:ethyl acetate:hexane as eluent. This column was divided into 12 equal parts; fraction 10 gave 5 g of product. Recrystallization of fraction 10 from diethyl ether gave 3.0 g of the desired product, m.p. 108°–110° C.

EMBODIMENT 14

(±)-2-exo-Benzyloxy-1-methyl-4-(1-methyl-1-phenylsulfonyl)ethyl)-7-oxabicyclo[2.2.1]heptane Following procedures similar to those described in Embodiments 2 and 6, (±)-2-exo-hydroxy-1-methyl-4-(1-methyl-1-phenylsulfonyl)ethyl)-7-oxabicyclo[2.2.1-]heptane was treated with benzyl chloride to yield the desired product as a solid, m.p. 94°–96° C.

EMBODIMENT 15

(±)-4-Methyl-1-(1-methyl-1-(methylthio)ethyl)-3-cyclohexen-1-ol

To a stirred solution of 15.2 g of 2,2,6-trimethyl-1-oxaspiro(2.5)oct-5-ene in 100 ml of N,N-dimethylacetamide was added 4.4 g of 60% sodium hydride. The mixture was cooled to 5°–10° C. and saturated with methyl mercaptan. Stirring was continued while heating the reaction mixture to 100° C. over a two and one-half hour period. After an additional hour at 100° C., the reaction mixture was poured into water and extracted twice with n-pentane. The combined extracts were washed with water, dried and Claisen-distilled to give 15.8 g of the desired product, b.p. 83°–85° C. (0.2 mm).

EMBODIMENT 16

(±)-2-exo-(Benzyloxy)-1-methyl-4-(1-methyl-1-(methylsulfonyl)ethyl)-7-oxabicyclo[2.2.1]heptane Following procedures similar to those described in Embodiment 13, (±)-4-methyl-(1-methyl-1-(methylthio)ethyl)-3-cyclohexen-1-ol was treated with vanadium-(IV) bis(2,4-pentanedionate) oxide and tert-butyl hydroperoxide followed by p-toluenesulfonic acid to obtain (±)-2-exo-hydroxy-1-methyl-4-(1-methyl-1-(methylsulfonyl)ethyl)-7-oxabicyclo[2.2.1]heptane. This intermediate product was treated with benzyl chloride by procedures similar to those described in Embodiments 2 and 6 to yield the desired product as an amber oil.

EMBODIMENT 17

(±)-4-Methyl-(1-(1-chloro-1-methylethyl))-3-cyclohexen-1-ol

To a stirred solution of 15.2 g of 2,2,6-trimethyl-1-oxaspiro(2.5)oct-5-ene in 200 ml of diethyl ether held at −10° C. was added dropwise 32 ml of 3.8N ethereal hydrochloric acid. After one hour at 0°–5° C., the mixture was washed with three 50 ml portions of water, dried and distilled to give 14.5 g of the desired product, b.p. 70°–75° C. (0.4 mm).

EMBODIMENT 18

(±)-2-exo-(Benzyloxy)-4-(1-chloro-1-methylethyl)-1-methyl-7-oxabicyclo[2.2.1]heptene Following procedures similar to those described in Embodiments 5 and 13, (±)-4-methyl-(1-(1-chloro-1-methylethyl))-3-cyclohexen-1-ol was treated with vanadium(IV) bis(2,4-pentanedionate) oxide and tert-butyl hydroperoxide followed by p-toluenesulfonic acid to obtain (±)-2-exo-hydroxy-4-(1-chloro-1-methylethyl)-1-methyl-7-oxabicyclo[2.2.1]heptane. This intermediate product was treated with benzyl chloride by procedures similar to those described in Embodiments 2 and 6 to yield the desired product, b.p. 120°–122° C. (0.15 mm).

EMBODIMENT 19

(±)-1-Hydroxy-alpha,alpha,4-trimethyl-3-cyclohexene-1-acetonitrile

To a stirred mixture of 7.0 g of zinc dust (washed twice with 10% hydrochloric acid, then successively with water, acetone and diethyl ether, and dried overnight at 60° C. in a vacuum oven), 0.45 g of mercuric chloride and 4 ml of tetrahydrofuran was added dropwise over 45 minutes at 20°–25° C. a mixture of 9.7 g of 4-methyl-3-cyclohexen-1-one, 13.7 g of alpha-bromoisobutyronitrile and 25 ml of tetrahydrofuran. After an additional hour at 25° C., the reaction mixture was cooled to 5°–10° C. and treated dropwise with 50 ml of cold 10% sulfuric acid. To this was added 100 ml of methylene chloride, and the mixture was filtered. The filtrate was diluted with 100 ml of water and extracted twice with 100 ml portions of methylene chloride. The combined methylene chloride extracts were washed with bicarbonate, dried and Claisen-distilled to give 11.3 g of the desired product, b.p. 92°–102° C. (0.25 mm).

EMBODIMENT 20

(±)-2-exo-(Benzyloxy)-4-(1-cyano-1-methylethyl)-1-methyl-7-oxabicyclo[2.2.1]heptane By procedures similar to those described in Embodiments 5 and 13, (±)-1-hydroxy-alpha,alpha-4-trimethyl-3-cyclohexene-1-acetonitrile was treated with vanadium(IV) bis(2,4-pentanedionate) oxide and tert-butyl hydroperoxide followed by p-toluenesulfonic acid to obtain (±)-2-exo-hydroxy-1-methyl-4-(1-cyano-1-methylethyl)-7-oxabicyclo[2.2.1]heptane. This intermediate product was treated with benzyl chloride by procedures similar to those described in Embodiments 2 and 6 to yield the desired product, b.p. 139°–140° C. (0.1 mm).

EMBODIMENT 21

(±)-2-exo-(2,6-(Dichlorobenzyloxy)-4-(1-cyano-1-methylethyl)-1-methyl-7-oxabicyclo[2.2.1]heptane By procedures similar to those described in Embodiments 5 and 13, 1-hydroxy-alpha,alpha, 4-trimethyl-3-cyclohexene-1-acetonitrile was treated with vanadium-(IV) bis(2,4-pentanedionate) oxide and tert-butyl hydroperoxide followed by p-toluenesulfonic acid to obtain (±)-2-exo-hydroxy-4-(1-cyano-1-methylethyl)-1-methyl-7-oxabicyclo[2.2.1]heptane. This intermediate product was treated with 2,6-dichlorobenzyl chloride by procedures similar to those described in Embodiments 2 and 6 to yield the desired product, b.p. 162°–165° C. (0.15 mm).

EMBODIMENT 22

(±)-1-(1-hydroxy-1-methylethyl)-4-methyl-3-cyclohexen-1-ol

A mixture of 26.0 g of 2,2,6-trimethyl-1-oxaspiro(2.5)oct-5-ene and 250 ml of 1% sulfuric acid was stirred magnetically for 20 hours, then extracted with four 100 ml portions of methylene chloride. The combined methylene chloride extracts were washed, dried, concentrated and Claisen-distilled to give 22.4 g of the desired product, b.p. 78°–81° C. (0.15 mm).

EMBODIMENT 23

(±)-2-exo-(Benzyloxy)-4-(1-hydroxy-1-methylethyl)-1-methyl-7-oxabicyclo[2.2.1]heptane By procedures similar to those described in Embodiment 5, (±)-1-(1-hydroxy-1-methylethyl)-4-methyl-3-cyclohexen-1-ol was treated with vanadium(IV) bis(2,4-pentanedionate) oxide and tert-butyl hydroperoxide followed by p-toluenesulfonic acid to obtain (±)-2-exo-hydroxy-4-(1-hydroxy-1-methylethyl)-1-methyl-7-oxabicyclo[2.2.1]heptane. This intermediate product was treated with benzyl chloride by procedures similar to those described in Embodiments 2 and 6 to yield the desired product, b.p. 114°–115° C. (0.1 mm).

EMBODIMENT 24

(±)-4-Methyl-1-(1-methoxy-1-methylethyl)-3-cyclohexen-1-ol

To a stirred solution of 0.8 g of p-toluenesulfonic acid in 125 ml of methanol held at 3°–5° C. was added dropwise over 0.5 hour a solution of 15.2 g of 2,2,6-trimethyl-1-oxaspiro(2.5)oct-5-ene in 25 ml of methanol. After an additional 2 hours at 5° C. and 2 hours at 5°–20° C., the mixture was treated with 2 ml of 15% sodium hydroxide and concentrated at a water pump at below 60° C. The residue was dissolved in methylene chloride, washed, dried and Claisen-distilled to give 15.6 g of the desired product, b.p. 70° C. (0.2 mm).

EMBODIMENT 25

(±)-2-exo-(Benzyloxy)-4-(1-methoxy-1-methylethyl)-1-methyl-7-oxabicyclo[2.2.1]heptane By procedures similar to those described in Embodiment 5, 1-(1-methoxy-1-methylethyl)-4-methyl-3-cyclohexen-1-ol was treated with vanadium(IV) bis(2,4-pentandionate) oxide and tert-butyl hydroperoxide followed by p-toluenesulfonic acid to obtain (±)-2-exo-hydroxy-4-(1-methoxy-1-methylethyl)-1-methyl-7-oxabicyclo[2.2.1]heptane. This intermediate was treated with benzyl chloride by procedures similar to those described in Embodiments 2 and 6 to yield the desired product, b.p. 110°–115° C. (0.1 mm).

EMBODIMENT 26

(±)-2-exo-(Benzyloxy)-4-(1-ethoxy-1-methylethyl)-1-methyl-7-oxabicyclo[2.2.1]heptane By procedures similar to those described in Embodiments 24 and 25, 2,2,6-trimethyl-1-oxaspiro(2.5)oct-5-ene was treated with ethanol in the presence of p-toluenesulfonic acid to obtain 1-(1-ethoxy-1-methylethyl)-4-methyl-3-cyclohexen-1-ol. This alcohol was treated with vanadium(IV) bis(2,4-pentandionate) oxide and tert-butyl hydroperoxide followed by p-toluenesulfonic acid to obtain (±)-2-exo-hydroxy-4-(1-ethoxy-1-methylethyl)-1-methyl-7-oxabicyclo[2.2.1]heptane. This intermediate was treated with benzyl chloride to yield the desired product, b.p. 120°–125° C. (0.2 mm).

EMBODIMENT 27

(±)-2-exo-(Benzyloxy)-4-(1-isopropoxy-1-methylethyl)-1-methyl-7-oxabicyclo[2.2.1]heptane By procedures similar to those described in Embodiments 24 and 25, 2,2,6-trimethyl-1-oxaspiro(2.5)oct-5-ene was treated with isopropyl alcohol in the presence of p-toluenesulfonic acid to obtain 1-(1-isopropoxy-1-methylethyl)-4-methyl-3-cyclohexen-1-ol. This alcohol was treated with vanadium(IV) bis(2,4-pentandionate) oxide and tert-butyl hydroperoxide followed by p-toluenesulfonic acid to obtain (±)-2-exo-hydroxy-4-(1-isopropoxy-1-methylethyl)-1-methyl-7-oxabicyclo[2.2.1]heptane. This intermediate was treated with benzyl chloride to yield the desired product, b.p. 120°–130° C. (0.2 mm).

EMBODIMENT 28

3,4-cis-Epoxy-1-isopropyl-4-methylcyclohexanol

To a solution of 30.8 g of (±)-terpinen-4-ol in 250 ml of toluene containing 1.0 g of vanadium(IV) bis(2,4-pentanedionate) oxide held at 45° C. was added 22.0 g of 90% tert-butyl hydroperoxide. Cooling was used to maintain the reaction temperature at 45°–50° C. for several minutes. After two hours longer at the same temperature, the mixture was cooled, washed with 1N sodium hydroxide, dried and Claisen-distilled to give 30.6 g of the desired product, b.p. 75° C. (2 mm). The NMR was the same as that reported in the literature.

EMBODIMENT 29

2-exo-hydroxy-1-methyl-4-isopropyl-oxabicyclo[2.2.1]heptane

Following procedures similar to those described in Embodiment 1 above, the epoxy-alcohol prepared as described in Embodiment 28 above was treated with p-toluenesulfonic acid to give the desired product.

EMBODIMENT 30

4-Methyl-3-cyclohexen-1-one

A mixture of 352 g of p-methyldihydroanisole (85% purity), 1350 ml of diethyl ether, 28 g of oxalic acid and 900 ml of water was stirred mechanically for 21 hours at 25° C. The aqueous layer was separated and extracted twice with ether. The combined ether solutions were washed with sodium bicarbonate, dried, concentrated and Claisen-distilled to give 250 g of 4-methyl-3-cyclohexen-1-one, b.p. 63°–65° C. (13 mm).

EMBODIMENT 31

2,2,4-Trimethyl-3-cyclohexen-1-one

To a 500 ml 3-neck, round-bottom flask were charged 37.5 g of 88% purity 4-methyl-3-cyclohexen-1-one, 100 ml of ether, 89.5 g of methyl iodide and 0.3 g of "Aliquot 336" (methyltrioctylammonium chloride). This mixture was stirred mechanically at ambient temperature and treated with 30 g of granular sodium hydroxide. After 20 minutes at gentle reflux (no cooling used), heat was applied to maintain the reflux for 2 hours longer. The cooled mixture was diluted with ether and treated with water to dissolve the suspended salts. The ether was separated and the aqueous layer was extracted with ether. The combined ether extracts were washed, dried, concentrated and Claisen-distilled to give 36.5 g of the desired product, b.p. 60° C. (10 mm).

EMBODIMENT 32

2,2,4-Trimethyl-3-cyclohexen-1-ol

To a stirred solution of 27.6 g of the ketone of Embodiment 31 above in 250 ml of ethanol was added portionwise 7.6 g of sodium borohydride. A cooling bath was used to hold the temperature at 25°–30° C. After 2 hours the mixture was poured into water and extracted three times with methylene chloride. The combined methylene chloride extracts were washed, dried, concentrated and stabilized at 25° C. and 0.1 mm to give 27.7 g of the desired product.

EMBODIMENT 33 cis-3,4-Epoxy-2,2,4-trimethylcyclohexanol

A solution of 27.7 g of the alcohol of Embodiment 32 above in 250 ml of methylene chloride was treated with 1.0 g of vanadium(IV) bis(2,4-pentanedioate) oxide and 22.0 g of 90% tert-butylhydroperoxide. After stirring overnight at 25° C., the mixture was washed with 1N sodium hydroxide, dried and Claisen-distilled to give 23.7 g of the desired product, b.p. 58°–61° C. (1 mm).

EMBODIMENT 34

1,3,3-Trimethyl-7-oxabicyclo[2.2.1]heptan-2-exo-ol

To a stirred solution of 20.0 g of the epoxy-alcohol of Embodiment 33 above in 200 ml of methylene chloride at 25° C. was added dropwise over 20 min a solution of 0.4 g of p-toluenesulfonic acid in 5 ml of glyme. After 1 hour longer the solution was washed with dilute potassium carbonate, dried, concentrated, and Claisen-distilled to give 11.1 g, b.p. 55°–77° C. (1.0–0.1 mm). This was redistilled through a micro Vigreaux column to give 2.8 g of the desired product, b.p. 77°–80° C. (3.0 mm).

EMBODIMENT 35

2-exo-Benzyloxy-1,3,3-trimethyl-7-oxabicyclo[2.2.1]heptane

A stirred solution of 2.2 g of the product of Embodiment 34 above in 30 ml of N,N-dimethylacetamide was treated with 0.8 g of 50% sodium hydride and held at 80°–85° C. for 0.5 hr. The mixture was cooled to 25° C. and 2.0 g of benzyl chloride was added. An exothermic reaction carried the temperature to 40°–45° C. Heat was applied to hold the temperature at 50°–55° C. for 0.5 hr. The cooled solution was poured into water and extracted twice with hexane. The combined hexane extracts were washed, dried, concentrated and micro-Claisen-distilled to give 2.3 g of the desired product, b.p. 97°–99° C. (0.1 mm). A forecut of 0.6 g of the desired product, b.p. 90°–97° C. (0.1 mm) was also obtained.

EMBODIMENT 36

1,2,2,4-Tetramethyl-3-cyclohexen-1-ol

To a stirred solution of 80 ml of 2.9M methyl magnesium chloride (in tetrahydrofuran) in 200 ml of dry tetrahydrofuran was added dropwise at 25°–30° C. a solution of 27.6 g of ketone of Embodiment 31 above in 30 ml of tetrahydrofuran. After 1 hour longer at 25° C. and 1 hour at 45°–50° C., the mixture was cooled and treated carefully with 50 ml of saturated ammonium sulfate. The mixture was extracted twice with diethyl ether and the combined ether extracts were dried, concentrated and distilled through a micro Vigreaux column to give 12.5 g (A), b.p. 115°–125° C. (100 mm), which was mainly unchanged ketone starting material and 11.1 g (B), b.p. 125°–115° C. (100–50 mm), which was the desired product of 81% purity. The final cut of 2.0 g (C), b.p. 115°–120° C. (50–20 mm) was the desired product of 87% purity.

EMBODIMENT 37

1,3,3,4-Tetramethyl-7-oxabicyclo[2.2.2]heptan-2-exo-ol

To a stirred solution of 11.1 g of 81% purity, 1,2,2,4-tetramethyl-3-cyclohexan-1-ol and vanadium(IV) bis(2,4-pentanedioate) oxide in 100 ml of methylene chloride was added 8.0 g of 90% tert-butyl hydroperoxide. The exothermic reaction produced a gentle reflux within 10 minutes. After 1.5 hours longer at reflux, the solution was cooled, dried with magnesium sulfate for 0.5 hour and filtered to give 125 ml of solution. This was stirred at 25° C. and treated dropwise over 15 minutes with a solution of 0.25 g of p-toluenesulfonic acid in 3.2 ml of glyme. After 1.5 hours longer, the solution was washed with dilute carbonate, dried, concentrated, and Claisen-distilled to give 8.5 g of 66% purity (GLC)

product, b.p. 60°–80° C. (10–1 mm). Recrystallization from concentrated pentane solution at −15° C. gave 2.8 g of the desired product, m.p. 58°–62° C.

EMBODIMENT 38

2-exo-Benzyloxy-1,3,3,4-tetramethyl-7-oxabicyclo[2.2.1]heptane

Following procedures similar to those described in Embodiment 35, the desired product was prepared by treating the exo-alcohol of Embodiment 37 above with benzyl chloride to yield the ether, b.p. 95°–100° C. (0.2 mm).

EMBODIMENT 39

2,2,4,6,6-Pentamethyl-3-cyclohexen-1-one

To a stirred solution of 27.6 g of the ketone of Embodiment 31 above and 62.5 g of methyl iodide in 350 ml of tetrahydrofuran was added portionwise with cooling at 25°–35° C. 20.2 g of 50% sodium hydride. The reaction was completed by refluxing for an hour longer.

The cooled mixture was filtered and the filter cake was washed with tetrahydrofuran. The filtrate was concentrated to low volume and poured into water. Three extractions with methylene chloride, followed by washing, drying, concentration and Claisen-distillation, gave 25.6 g of the desired product.

EMBODIMENT 40

2-exo-Benzyloxy-1,3,3,4,5,5-hexamethyl-7-oxabicyclo[2.2.1]heptane

Following procedures described in Embodiments 31–38, the desired product was prepared by treating the ketone of Embodiment 39 above with methyl magnesium chloride to yield the corresponding alcohol which is epoxidized and cyclized to the oxabicycloalkanol followed by treatment with benzyl chloride to yield the ether, b.p. 110°–115° C. (0.1 mm).

EMBODIMENT 41

1-Ethoxycarbonylmethyl-4-methyl-3-cyclohexen-1-ol

To a stirred mixture of 26.0 g of zinc dust (washed twice with 10% hydrochloric acid, then successively with water, acetone and ether and dried overnight at 60° C. in a vacuum oven), 2.0 g of iodine and 40 ml of benzene was added rapidly at 65°–75° C. a solution of 22.0 g of 4-methyl-3-cyclohexen-1-one of Embodiment 30 above and 62.6 g of ethyl bromoacetate in 400 ml of benzene. After 5 hours at reflux the mixture was cooled to <10° C. and treated dropwise with 300 ml of 10% acetic acid. After 15 minutes, the layers were separated and the aqueous layer was extracted twice with 150 ml of benzene. The combined organic layers were washed successively with water, sodium bicarbonate solution and water. After drying and concentration, Claisen distillation gave 33.0 g of the desired product, b.p. 82°–84° C. (0.5 mm).

EMBODIMENT 42

4-Ethoxycarbonylmethyl-2-exo-hydroxy-1-methyl-7-oxabicyclo[2.2.1]heptane

To a stirred, refluxing solution of 46.2 g of alcohol of Embodiment 41 above and 1.2 g of vanadium(IV) bis(2,4-pentanedionate) oxide in 400 ml of methylene chloride as was added dropwise 25.3 g of 90% tert-butyl hydroperoxide. After 2 hours longer at reflux, the solution was cooled, dried over magnesium sulfate, and filtered through Celite. The stirred filtrate was treated with 12 ml of glyme containing 1.0 g of p-toluenesulfonic acid. After 18 hours at 25° C., the mixture was washed with dilute carbonate and dried. Vacuum-concentration at 50° C. gave 52.3 g of dark amber oil. GLC analysis indicated the presence of 56% of desired product.

Purification via HPLC using ethyl acetate as eluent gave 16.8 g of the desired product an an oil.

EMBODIMENT 43

2-exo-Benzyloxy-4-benzyloxycarbonyl-methyl-1-methyl-7-oxabicyclo[2.2.1]heptane

To a stirred solution of 4.3 g of alcohol of Embodiment 42 above in 15 ml of ethanol was added a solution of 0.9 g of sodium hydroxide in 3 ml of water. After 24 hours at 25° C., the mixture was vacuum-concentrated at 30° C. (<1 mm). The residue was dissolved in 30 ml of dimethylacetamide and treated with 1.0 g of 50% sodium hydride. After 6 hours at 25° C., 5.5 g of benzyl chloride was added, and stirring was continued for 4 days. The mixture was poured into water, extracted 3 times with methylene chloride, and the combined methylene chloride extracts were washed, dried and concentrated to a residue of 8.1 g. This oil was purified by column chromatography to give 2.6 g of desired product as an oil.

EMBODIMENT 44

2-exo-Benzyloxy-4-carboxymethyl-1-methyl-7-oxabicyclo-[2.2.1]heptane

To a stirred solution of 3.1 g of ether of Embodiment 43 above in 15 ml of ethanol was added a solution of 0.6 g of sodium hydroxide in 2.5 ml of water. After 19 hours at 25° C., the mixture was acidified to Congo Red paper using 6N hydrochloric acid. After dilution with 150 ml of methylene chloride, the organic layer was washed twice with 25 ml portions of water. The dried methylene chloride solution was concentrated to a residue of 2.8 g. This was purified by preparative plate chromatography to give 1.7 g of the desired product as an oil.

EMBODIMENT 45

(−)-2-exo-Hydroxy-1-methyl-4-isopropyl-7-oxabicyclo[2.2.1]heptane

The procedure of Embodiment 1 was repeated using (−)-terpinen-4-ol ($[\alpha]_D - 28°$ (CHCL$_3$)). The distilled product was recrystallized from hexane to give the subject material having m.p. 83°–85° C. and $[\alpha]_D + 0.4°$ (CHCL$_3$).

EMBODIMENT 46

(−)-2-exo-(2-Methylbenzyloxy)-1-methyl-4-isopropyl-7-oxabicyclo[2.2.1]heptane

To a stirred solution of 2.6 g of (−)-2-exo-hydroxy-1-methyl-4-isopropyl-7-oxabicyclo[2.2.1]heptane of Embodiment 45 above in 20 ml of N,N-dimethylacetamide was added 0.8 g of 50% sodium hydride (washed with hexane). After 1 hour at 60° C., the mixture was cooled to 25° C., treated with 2.3 g of 2-methylbenzyl chloride, and allowed to stir overnight at ambient temperature. After 0.5 hour at 50° C., the mixture was cooled, poured into water and extracted twice with hexane. The combined hexane extracts were washed, dried, concentrated and Claisen-distilled to give 3.5 g of the subject compound, b.p. 114°–116° C. (0.1 mm); $[\alpha]_D - 73°$ (CHCL$_3$).

EMBODIMENT 47

3,4-cis-Epoxy-1-isopropyl-4-methylcyclohexanol

To a stirred, refluxing mixture of 15.4 g of terpinen-4-ol, 150 ml of propylene oxide and 0.3 g of vanadium(IV) bis(2,4-pentanedionate) oxide was added dropwise over 15 minutes 5.4 g of 70% hydrogen peroxide. After 45 minutes longer, the mixture was vacuum-concentrated at 60° C. (bath). The residue was shaken with a mixture of pentane and water and the dried pentane layer was vacuum-concentrated to a residue of 11.2 g. This product was identified as 3,4-cis-epoxy-1-isopropyl-4-methylcyclohexanol by GLC and infrared comparisons with the material described in Embodiment 28.

EMBODIMENT 48

(±)-2-exo-(2-Methylbenzyloxy)-1-methyl-4-isopropyl-7-oxabicyclo[2.2.1]heptane A 12 l flask was charged under nitrogen with 264 g of 50% sodium hydride (previously washed with hexane) followed by 3 l of dry dimethylformamide. The resulting mixture was heated to 60° C. and a solution of 850 g of (±)-2-exo-hydroxy-1-methyl-4-isopropyl-7-oxabicyclo[2.2.1]heptane in 1.5 l of dimethylformamide was added over 3 hours while maintaining the reaction mixture at 60°–70° C. Then the reaction mixture was cooled to 20° C. and 730.6 g of 2-methylbenzyl chloride was added over 1½ hours while cooling the reaction mixture to 20°–25° C. The reaction mixture was stirred at room temperature for 16 hours. The resulting mixture was poured into 20 l of water, acidified with concentrated hydrochloric acid and extracted three times with 3.5 l of hexane. The combined extracts were back-washed with 3 l of water, dried (MGSO$_4$), filtered and evaporated to dryness to yield 1280 g of the desired product.

EMBODIMENT 49

(±)-2-exo-Hydroxy-1-methyl-4-isopropyl-7-oxabicyclo[2.2.1]heptane

A dry flask was charged with 15 kg of terpinene-4-ol and 50 l of toluene followed by 78 g of triethylamine and 195 g of vanadium(IV) bis(2,4-pentanedionate) oxide. The mixture was heated to reflux, and 11.25 kg of 90% tert-butyl hydroperoxide in 11 l of toluene was added over 45 minutes. The mixture was stirred at ambient temperature for one hour longer, then cooled, washed and dried. The product, cis-epoxy alcohol in toluene, was treated with 54 g of 96% sulfuric acid mixed with 600 cc of mole sieve and dried tetrahydrofuran. The mixture was stirred for 16 hours. The resulting solution was washed successively with water, aqueous 5% sodium carbonate and then water, and concentrated to give the desired product.

I claim:

1. A process for the preparation of a 2-exo-hydroxy-7-oxa-bicyclo[2.2.1]heptane which comprises treating a cis-epoxycyclohexanol with acid in an inert solvent and recovering a 2-exo-hydroxy-7-oxa-bicyclo[2.2.1]heptane.

2. A process according to claim 1 wherein a 2-exo-hydroxy-7-oxabicyclo[2.2.1]heptane of the formula I

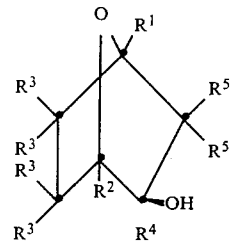

wherein $R^1$ is a hydrogen atom; or is an alkyl group containing from 1 to 10 carbon atoms optionally substituted by up to 3 halogen atoms, each having an atomic number of from 9 to 35, inclusive, or by a hydroxy group, a cyano group or an alkoxy group containing from 1 to 4 carbon atoms, a $C_{1-6}$ alkylsulfonyl group, a $C_{6-10}$ arylsulfonyl group, a $C_{7-11}$ aralkylsulfonyl group, an azido group, a $C_{1-6}$ alkoxycarbonyl group, a hydroxycarbonyl group, a phosphoryl group, a phosphoryloxy group, an amine oxide group, a carbamoyl group, a thiocarbamoyl group in which each nitrogen atom is substituted by hydrogen or by 1 or 2 alkyl groups containing from 1 to 4 carbon atoms; or is an aryl or aralkyl group, each containing from 6 to 11 carbon atoms, and 1 to 4 carbons in the alkyl portion, each optionally ring-substituted by one or more substituents independently selected from a halogen atom, each having an atomic number of from 9 to 35, inclusive, or by an alkyl or alkoxy group containing from 1 to 2 carbon atoms, each optionally substituted by one or more halogen atoms, each having an atomic number of from 9 or 17; or $R^1$ is a group $CO_2R^6$ or $CON(R^6)_2$ in which $R^6$ is a hydrogen atom, or an alkyl group containing from 1 to 6 carbon atoms;

$R^2$ is a hydrogen atom or a straight-chain alkyl group containing from 1 to 6 carbon atoms;

each $R^3$ is independently selected from a hydrogen atom; a chlorine atom; a bromine atom; or an alkyl group containing from 1 to 4 carbon atoms, optionally substituted by up to 3 halogen atoms, each having an atomic number of from 9 to 35, inclusive; or two of $R^3$ when located on adjacent carbon atoms together form an epoxide ring or a carbon-carbon bond;

$R^4$ is a hydrogen atom; or an alkyl group containing from 1 to 4 carbon atoms optionally substituted by up to 3 halogen atoms having an atomic number of from 9 to 35, inclusive;

each $R^5$ is independently selected from a hydrogen atom; or an alkyl group containing from 1 to 4 carbon atoms, optionally substituted by up to 3 halogen atoms having an atomic number of from 9 to 35, inclusive; or a hydroxy group containing from 1 to 4 carbon atoms; is prepared by treating a cis-epoxy-alcohol of the formula

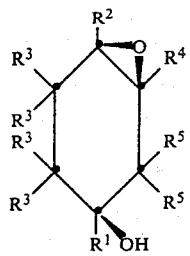

wherein each $R^2$, $R^1$, $R^3$, $R^4$ and $R^5$ has the above defined meanings with an acid catalyst.

3. A process according to claim 2 wherein $R^2$ is a straight-chain alkyl group containing from 1 to 6 carbon atoms, $R^1$ is an alkyl group containing from 1 to 6 carbon atoms optionally substituted by up to 3 halogen atoms selected independently from fluorine, chlorine or bromine atoms or by OH, CN, an alkoxy group containing from 1 to 4 carbon atoms, a $C_{1-6}$ alkylsulfonyl group, a phenylsulfonyl group, a benzylsulfonyl group or is an aryl or aralkyl group each containing from 6 to 10 carbon atoms and 1 or 2 carbon atoms in any alkyl portion, optionally substituted by one or more substituents independently selected from a halogen atom having an atomic number of from 9 to 35, inclusive. or by an alkyl or alkoxy group containing from 1 to 2 carbon atoms each optionally substituted by one or more halogen atoms having an atomic number of from 9 or 17, and each $R^3$, $R^4$ and $R^5$ is a hydrogen atom.

4. A process according to claim 2 wherein the solvent is toluene.

5. A process according to claim 2 wherein the solvent is methylene chloride.

6. A process according to claim 2 wherein the catalyst is a mineral acid.

7. A process according to claim 6 wherein the catalyst is sulfuric acid.

8. A process according to claim 2 wherein the acid is an organic acid.

9. A process according to claim 8 wherein the organic acid is a sulfonic acid.

10. A process according to claim 9 wherein the sulfonic acid is p-toluene sulfonic acid.

11. A process according to claim 3 wherein 4-methyl-1-iso-propyl-3,4-cis-epoxycyclohexan-1-ol is treated with acid to yield 2-exo-hydroxy-1-methyl-4-isopropyl-7-oxabicyclo[2.2.1]heptane.

12. A process according to claim 3 wherein 1,4-diethyl-3,4-cis-epoxycyclohexan-1-ol is treated with acid to yield 2-exo-hydroxy-1,4-diethyl-7-oxabicyclo[2.2.1]heptane.

13. A process according to claim 1 wherein the cis-epoxycyclohexanol is prepared by treating a corresponding 3-cyclohexen-1-ol with an oxidizing agent which will produce the cis-epoxy alcohol, in an inert solvent.

14. A process according to claim 13 wherein the oxidizing agent is a peroxide.

15. A process according to claim 14 conducted in the presence of a vanadium catalyst.

16. A process according to claim 15 wherein the vanadium catalyst is an organic complex of vanadium.

17. A process according to claim 15 wherein the oxidation is conducted with tert-butyl hydroperoxide in the presence of vanadium(IV) bis(2,4-pentanedionate) oxide.

18. A process according to claim 13 wherein the treatment with the oxidizing agent and with the acid are conducted concurrently.

* * * * *